United States Patent [19]

Hansen et al.

[11] Patent Number: 4,551,214
[45] Date of Patent: Nov. 5, 1985

[54] PHOTOCHEMICAL PREPARATION OF PREVITAMIN D

[75] Inventors: Hans-Jürgen Hansen, Riehen; Karlheinz Pfoertner, Basel, both of Switzerland

[73] Assignee: Hoffmann-La Roche Inc., Nutley, N.J.

[21] Appl. No.: 620,418

[22] Filed: Jun. 14, 1984

[30] Foreign Application Priority Data

Jul. 1, 1983 [CH] Switzerland .................. 3637/83

[51] Int. Cl.$^4$ ............................................. B01J 19/12
[52] U.S. Cl. ............................................. 204/159
[58] Field of Search ........................................ 204/159

[56] References Cited

U.S. PATENT DOCUMENTS 3,575,831  4/1971  Pfoertner et al. .................. 204/159

*Primary Examiner*—Howard S. Williams
*Attorney, Agent, or Firm*—Jon S. Saxe; Bernard S. Leon; William G. Isgro

[57] ABSTRACT

Compounds of the formula

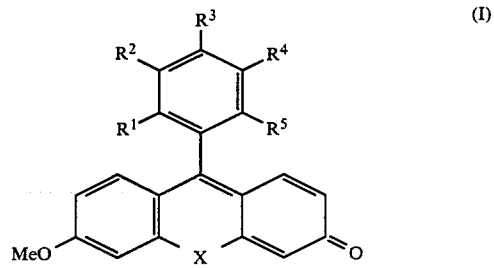

(I)

wherein $R^1$-$R^4$ is hydrogen or chlorine, $R^5$ is —COOMe or —SO$_3$Me, Me is an alkali metal cation and X is oxygen, sulfur or selenium, photosensitizers for the conversion of tachysterol into previtamin D are described. The tachysterol content in mixtures of previtamin D and tachysterol can be greatly reduced by visible light irradiation in the presence of such photosensitizers.

5 Claims, No Drawings

PHOTOCHEMICAL PREPARATION OF PREVITAMIN D

BRIEF SUMMARY OF THE INVENTION

The invention relates to compounds of the formula

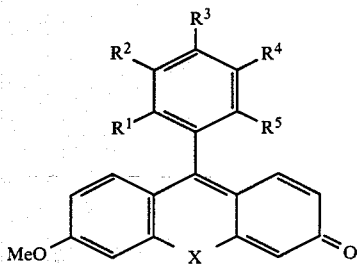

wherein $R^1$-$R^4$ is hydrogen or chlorine, $R^5$ is —COOMe or —SO$_3$Me, Me is an alkali metal cation and X is oxygen, sulfur or selenium, which are useful as photosensitizers for the conversion of tachysterol into previtamin D. The tachysterol content in mixtures of previtamin D and tachysterol can be greatly reduced by visible light irradiation in the presence of such photosensitizers.

DETAILED DESCRIPTION OF THE INVENTION

Vitamin D is prepared on a production scale by irradiating the provitamin 7-dehydrocholesterol or ergosterol and isomerizing the previtamin D formed in the irradiation. It is known that in the irradiation of the provitamin there are formed in addition to the previtamin other products, especially lumisterol and tachysterol, whereby the yield of the previtamin is reduced and a separation of the tachysterol is necessary.

An attempt has been made to improve the yield by carrying out the irradiation in two irradiation steps, with fluorenone being added to the initially obtained irradiation product and the mixture being irradiated again. According to this process tachysterol has been converted to some extent into previtamin D, but the process has the disadvantage that the fluorenone can be separated from the desired previtamin D only with difficulty.

It has now been found that previtamin D which is substantially free from tachysterol is obtained when a mixture of previtamin D and tachysterol is irradiated with light of a wavelength of about 400 nm to about 600 nm in the presence of a compound of the formula

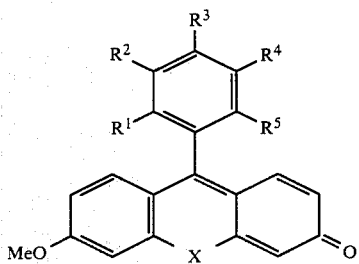

wherein $R^1$-$R^4$ is hydrogen or chlorine, $R^5$ is —COOMe or —SO$_3$Me, wherein Me is an alkali metal cation and X is oxygen, sulfur or selenium.

It has also been found that compounds of formula I are photosensitizers for the conversion of tachysterol into previtamin D. In the presence of compounds of formula I, tachysterol is converted into previtamin D to a substantially higher extent photosensitizably than in the case of the known process using fluorenone. Furthermore, the novel process can be carried out with visible light, so that UV-transmissive, expensive quartz glass apparatuses are unnecessary. A further advantage of the novel process lies in the fact that the photosensitizers, that is the compounds of formula I, are water-soluble and therefore can be extracted with water from solvents which are not miscible with water.

The irradiation can be carried out with any light source which emits between about 400 nm and about 600 nm, for example with a suitable mercury vapour lamp or with sunlight. A mercury high-pressure lamp such as a Hanau TQ 2020 lamp is preferably used.

The irradiation mixture is conveniently cooled, for example, to a temperature of about 15°-25° C., preferably 16°-17° C., during the irradiation.

Furthermore, it is convenient to eliminate UV-light between 300 and 340 nm which produces lumisterol. This can be achieved by arranging a filter which absorbs in this range, for example a glass filter or, preferably, a filter solution, between the light source and the irradiation mixture. Suitable filter solutions are aqueous solutions of iron sulfate and copper sulfate.

The previtamin D used in the process provided by the invention embraces precholecalciferol and preergocalciferol.

In a preferred embodiment of the process provided by the invention, there is used as the starting material the product which results in the irradiation of provitamin D, that is, 7-dehydrocholesterol or ergosterol, with UV-light between 240 and 300 nm and which contains large amounts of tachysterol in addition to unreacted provitamin D and previtamin D.

By means of the process provided by the invention mixtures of previtamin D and less than 3% of tachysterol can be obtained starting from mixtures which contain previtamin D and large amounts, for example more than 3%, especially 15–18%, of tachysterol.

The process provided by the invention can be carried out in a known manner for the preparation of vitamin D by irradiation.

As solvents there can be used all solvents which have hitherto been used as solvents for the photochemical preparation of vitamin D from dehydrocholesterol. Examples of such solvents are ethers such as tetrahydrofuran, dioxane and tert.butyl methyl ether. Preferred solvents are water-immiscible solvents, especially tert.butyl methyl ether.

In order to guarantee a sufficient solubilization of the photosensitizer in the reaction mixture, the photosensitizer, that is, the compound of formula I, is conveniently dissolved in an organic protic solvent which is miscible with the aforementioned solvents, for example, in methanol, and the solution is then added to the reaction mixture. The concentration of the photosensitizer present in the reaction is not critical, but this together with the layer thickness of the solution used for the irradiation influences the irradiation time. In the Examples given hereinafter the concentration of photosensitizer is chosen so that optimum yields are achieved with a layer thickness of 1 cm.

The compounds of formula I in which X is sulfur or selenium and $R^5$ is —SO$_3$Me when X is sulfur also form part of the invention. They can be prepared by reacting m,m'-selenodiphenol with a compound of the formula

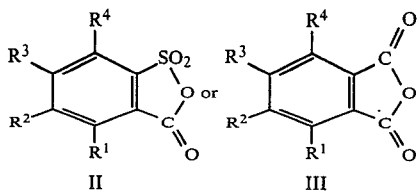

wherein $R^1$–$R^4$ are as previously described, or by reacting m,m'-thiodiphenol with a compound of formula II.

The reaction can be carried out by heating the reaction partners together, conveniently in the presence of an acid such as p-toluenesulfonic acid or trifluoromethanesulfonic acid. The reaction temperature is not critical; the reaction mixture is conveniently heated to a melt, for example to 80°–140° C. The compound of formula I can be extracted from the cooled melt with water at an alkaline pH and can be precipitated from the solution, optionally after purification, for example, by means of active carbon, by acidification.

Preferred compounds of formula I are those in which $R^1$–$R^4$ is hydrogen, $R^5$ is —COONa or —SO$_3$Na and X is sulfur or selenium.

The Examples which follow illustrate the invention in more detail:

EXAMPLE 1

A. A solution of 225 g of 7-dehydrocholesterol in 4.5 l of tert.butyl methyl ether was illuminated for 60 to 70 minutes with a high capacity mercury low-pressure lamp of 1.5 kW under an inert gas (argon or nitrogen) in a ring mantle vessel of quartz glass arranged cylindrically around the rod-shaped light source. The solution was circulated with the aid of a pump through the photoreactor and through an externally-situated reserve vessel which simultaneously served as the heat exchanger, whereby the temperature was held at 21°–22° C. There was obtained a reaction mixture containing 61.5% of 7-dehydrocholesterol, 20.4% of previtamin D$_3$; 0.2% of vitamin D$_3$; 16.8% of tachysterol and 1.1% of lumisterol.

B. 0.6 g of fluorescein disodium dissolved in 0.6 l of methanol was added to the solution obtained according to paragraph A. The resulting solution was pumped into a glass apparatus aperture equipped with 2 kW mercury high-pressure lamp. The light source was situated in the center of the apparatus and a ring mantle vessel having two chambers was arranged concentrically around the light source. The irradiation mixture was circulated with the aid of a pump through the outer chamber and through a reserve vessel, which simultaneously served as the heat exchanger and which has a temperature of 16°–17° C., situated outside the reactor. A filter solution having the following composition, which was also cooled externally, was pumped through the inner chamber situated between the light source and the irradiation mixture:
32.90 g of copper (II) sulfate pentahydrate,
1.05 g of iron (III) sulfate pentahydrate,
7.70 ml of sulfuric acid (95–98%),
993.40 ml of deionized water,
and this filter solution absorbed all light below 350 nm in a layer thickness of 1 cm. The sensitizer destroyed during the irradiation was replaced continuously, whereby 2.1 g of fluorescein disodium dissolved in 115 ml of methanol were added in the course of 5 hours. The photostationary state was attained after carrying out the illumination for 5 hours. The mixture obtained had the following composition:
61.5% of 7-dehydrocholesterol; 34% of previtamin D$_3$; 1% of vitamin D$_3$; 2.4% of tachysterol; and 1.1% of lumisterol.

EXAMPLE 2

A. A mixture having the following composition was obtained in analogy to Example 1A:
62.9% of 7-dehydrocholesterol; 19.6% of previtamin D$_3$; 0.5% of vitamin D$_3$; 16% of tachysterol and 1.0% of lumisterol in 4.5 l of tert.butyl methyl ether.

B. 0.66 g of disodium o-(6-hydroxy-3-oxy-3H-thiaxanthen-9-yl)-benzoate hydrate dissolved in 0.6 l of methanol was added to the mixture obtained in paragraph A and the resulting mixture was irradiated as described in Example 1B. The subsequent addition of additional sensitizer was not necessary and this was also the case in respect of the sensitizers used in the following Examples. The photostationary state was achieved after illuminating for 30 minutes and there was obtained a mixture having the composition 62.9% of 7-dehydrocholesterol; 33.1% of previtamin D$_3$; 1.2% of vitamin D$_3$; 1.8% of tachysterol; and 1.0% of lumisterol.

EXAMPLE 3

A. A mixture having the following composition was obtained in analogy to Example 1A.
62.0% of 7-dehydrocholesterol; 19.7% of previtamin D$_3$; 0.4% of vitamin D$_3$; 16.9% of tachysterol; and 1.0% of lumisterol in 4.5 l of tert.butyl methyl ether.

B. 0.74 g of disodium o-(6-hydroxy-3-oxo-3H-thioxanthen-9-yl)-benzenesulfonate dihydrate dissolved in 1.05 l of methanol was added to the mixture obtained in paragraph A and the resulting mixture was irradiated as described in Example 1B until the photostationary state was attained (21 minutes). There was obtained a mixture having the composition 62.0% of 7-dehydrocholesterol; 34.2% of previtamin D$_3$; 1.4% of vitamin D$_3$; 1.4% of tachysterol; and 1.0% of lumisterol.

EXAMPLE 4

A. A mixture having the following composition was obtained in analogy to Example 1A:
62.0% of 7-dehydrocholesterol; 19.6% of previtamin D$_3$; 0.5% of vitamin D$_3$; 16.8% of tachysterol; and 1.1% of lumisterol in 4.5 l of tert.butyl methyl ether.

B. 0.73 g of o-(6-hydroxy-3-oxo-3H-selenoxanthen-9-yl)-benzoic acid.1 acetone dissolved in 0.3 l of methanol and 0.18 g of sodium methylate dissolved in 0.3 l of methanol were added to the mixture obtained in paragraph A and the resulting mixture was irradiated as described in Example 1B until the photostationary state was attained (15 minutes). There was obtained a mixture having the composition 62.0% of 7-dehydrocholesterol; 33.7% of previtamin D$_3$; 1.4% of vitamin D; 1.8% of tachysterol; and 1.1% of lumisterol.

EXAMPLE 5

A. A mixture having the following composition was obtained in analogy to Example 1A.
62.0% of 7-dehydrocholesterol; 19.7% of previtamin D$_3$; 0.3% of vitamin D$_3$; 16.9% of tachysterol; and 1.1% of lumisterol in 4.5 l of tert.butyl methyl ether.

B. 0.72 g of o-(6-hydroxy-3-oxo-3H-selenoxanthen-9-yl)-benzenesulfonic acid hydrate dissolved in 0.55 l of methanol and 0.18 g of sodium methylate dissolved in 0.5 l of methanol were added to the mixture obtained in paragraph A and the resulting mixture was irradiated as described in Example 1B until the photostationary state was attained (13 minutes). There was obtained a mixture having the composition 62.0% of 7-dehydrocholesterol; 33.5% of previtamin D$_3$; 1.9% of vitamin D$_3$; 1.5% of tachysterol; and 1.1% of lumisterol.

EXAMPLE 6

15.7 g of p-toluenesulfonic acid monohydrate were heated to 140° C. in order to remove the water of crystallization. 18 g of m,m'-thiodiphenol and 18.2 g of 2-sulfobenzoic anhydride were ground together and added under argon and while stirring to the hot anhydrous p-toluenesulfonic acid. The melt was held at 140° C. (internal temperature) and 0.1 Torr for 2 hours while stirring. After cooling, 16 g of sodium hydroxide dissolved in 0.3 l of water was added. After stirring at 50° C. for 1 hour, a solution of 0.09 l of water and 27 g of 95–97% sulfuric acid was added dropwise while stirring. In order to complete the precipitation, the mixture was cooled to about 5° C. in an ice-bath and then the very finely crystalline precipitate was filtered under suction. The filter cake was washed twice on the suction filter with icewater and pressed out well, thereafter triturated with 0.02 l of acetone and filtered under suction. This procedure was repeated twice. The dark brown finely crystalline residue was triturated twice with water, filtered under suction and rinsed on the suction filter with water. The yellow-brown crystals were dried at 80° C. for 20 hours in a water-jet vacuum. There were obtained 18 g of o-(6-hydroxy-3-oxo-3H-thioxanthen-9-yl)-benzenesulfonic acid of melting point above 300° C. (decomposition); absorption maximum of the disodium salt in methanol: $\lambda_{max}=524$ nm ($\epsilon=24430$).

EXAMPLE 7

5.0 g of m,m'-selenodiphenol and 5.85 g of phthalic anhydride were heated to 80° C. The melt was treated while stirring with 5 ml of trifluoromethanesulfonic acid, whereby the temperature in the reaction vessel rose to 120° C. and the mixture became black. The mixture was held for 1 hour in an oil-bath at about 90° C. (internal temperature), cooled, stirred at 60° C. for 2 hours with 100 ml of 2N sodium hydroxide, filtered and the residue was washed with 150 ml of water. 150 ml of 2N sulfuric acid were added dropwise to the filtrate within 40 minutes while stirring and the solution was left to stand at room temperature for 16 hours with the exclusion of light. The suspension was concentrated to about 250 ml, suction filtered and the residue was washed on the suction filter with 100 ml of water, removed from the filter with 250 ml of 3.5% sodium hydrogen carbonate solution, stirred at room temperature for 30 minutes and filtered over a filter aid. The filtrate was concentrated to about 300 ml and treated with 115 ml of 2N sulfuric acid for 1.25 hours while stirring. Thereafter, the solution was concentrated to about 200 ml, suction filtered and the residue was washed well firstly with water and subsequently with hexane. The residue was then dissolved in a small amount of methanol and the solution was placed on preparative layer chromatography (PLC) plates. After elution with dichloromethane/ethyl acetate (1:1), the zone recognized by color was scraped from the plates, suspended in cold methanol, filtered, the filtrate was evaporated to dryness and the procedure was repeated with acetone. There were obtained 2.33 g of o-(6-hydroxy-3-oxo-3H-selenoxanthen-9-yl)-benzoic acid.1 acetone in the form of red crystals of melting point 150° C. (decomposition). Acetone-free disodium salt in methanol: $\lambda_{max}=526$ nm ($\epsilon=18510$).

EXAMPLE 8

The water of crystallization was removed from 3.59 g of p-toluenesulfonic acid monohydrate at 140° C. and 0.1 Torr as described in Example 6. A mixture of 5 g of m,m'-selenodiphenol and 3.47 g of 2-sulfobenzoic anhydride was introduced into the hot melt of the p-toluenesulfonic acid. The mixture was held for 2.5 hours at 140° C. (internal temperature) and 0.01–0.05 Torr. After cooling, the semi-solid mass was dissolved at 50° C. in 150 ml of 25% ammonia, concentrated to about 75 ml, treated while stirring with water and the dark red solution was left to stand at room temperature for 16 hours with the exclusion of light. After the addition of about 1 g of active carbon, the mixture was filtered and the filter residue was rinsed with 200 ml of water. Thereafter, the solution was concentrated to about 400 ml at 60° C. and treated dropwise over a period of 1.8 hours while stirring with a mixture of 7.5 ml of 95–97% sulfuric acid in 30 ml of water. The product separated as a very fine red-brown precipitate which was filtered under suction after 0.5 hour and washed three times on the suction filter with 40 ml of diethyl ether each time. The crystallization was taken up in 150 ml of ethanol and the solution was evaporated to dryness at 50° C. in vacuo. Crude o-(6-hydroxy-3-oxo-3H-selenoxanthen-9-yl)-benzenesulfonic acid was obtained.

3.13 g of the crude product were dissolved in 200 ml of 25% ammonia, concentrated to 100 ml at 50° C. in vacuo and treated with 500 ml of water. The solution was filtered and the filtrate was concentrated to about 300 ml. Thereafter, 7.5 ml of 95–97% sulfuric acid in 30 ml of water were added over a period of 0.5 hour, the precipitate was filtered under suction over a paper filter after 16 hours, washed with 100 ml of water and with 100 ml of diethyl ether, taken up in 150 ml of ethanol and the suspension was evaporated completely at 60° C. in vacuo. There were obtained 2.70 g of product which still contained colored impurities according to thin-layer chromatography. This product was dissolved in 200 ml of 25% ammonia. The solution was evaporated to dryness, the salt was dissolved in 6 ml of water and treated while stirring with 60 ml of 2-propanol and subsequently with 80 ml of acetone. In order to complete the crystallization, 50 ml of solvent were removed by evaporation and the concentrated solution was left to stand at room temperature for 16 hours. The crystals were then filtered under suction and washed well with acetone. The salt was dissolved in 100 ml of water and the product was precipitated within 1.2 hour with a mixture of 7.5 ml of 95–97% sulfuric acid and 30 ml of water. After standing for 1 hour, the product was filtered under suction, washed well with diethyl ether and the crystallizate was dried for 20 hours at 50° C. in a water-jet vacuum. There were obtained 1.40 g of o-(6-hydroxy-3-oxo-3H-selenoxanthen-9-yl)-benzenesulfonic acid which was pure according to thin-layer chromatography. Disodium salt in methanol: $\lambda_{max}=533$ nm ($\epsilon=35540$).

We claim:

1. A process for the preparation of previtamin D which is substantially free from tachysterol, which process comprises irradiating a mixture of previtamin D and tachysterol with light of a wavelength of about 400 nm to about 600 nm in the presence of a compound of the formula

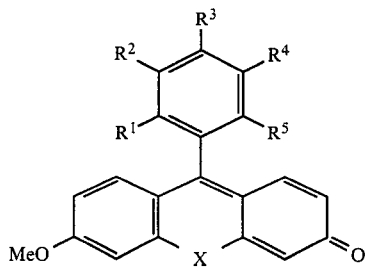
(I)

wherein $R^1$-$R^4$, independently, are hydrogen or chlorine, $R^5$ is —COOMe or —SO$_3$Me, Me is an alkali metal cation and X is oxygen, sulfur or selenium.

2. A process in accordance with claim 1, wherein a mixture which contains previtamin D and tachysterol and which is obtained by the UV-irradiation of provitamin D is irradiated.

3. A process in accordance with claim 1, wherein the light source is a mercury high-pressure lamp provided with a filter which eliminates the wavelengths below 365 nm.

4. A process in accordance with claim 3, wherein the filter is a liquid.

5. A process in accordance with claims 1, 2, 3 or 4, wherein a compound of formula I in which $R^1$-$R^4$ is hydrogen, $R^5$ is —COONa or —SO$_3$Na and X is sulfur or selenium is used.

* * * * *